United States Patent [19]

Miller

[11] 4,376,112

[45] Mar. 8, 1983

[54] ENCAPSULATED EFFICACIOUS ZINC PHOSPHIDE RODENTICIDE

[75] Inventor: George T. Miller, Lewiston, N.Y.

[73] Assignee: Occidental Chemical Corporation, Niagara Falls, N.Y.

[21] Appl. No.: 256,742

[22] Filed: Apr. 23, 1981

[51] Int. Cl.$^3$ ............................................. A01N 59/26
[52] U.S. Cl. ........................................ 424/17; 424/32; 424/78; 424/128
[58] Field of Search ...................... 424/78, 128, 32, 17

[56] References Cited

U.S. PATENT DOCUMENTS 2,957,804 10/1960 Shuyler .............................. 424/128

FOREIGN PATENT DOCUMENTS 1531677 5/1968 France .

OTHER PUBLICATIONS

Baker, R. *Controlled Release of Bioactive Materials*, N.Y., Academic Press, 1980, p. 277.

*Primary Examiner*—John F. Terapane
*Assistant Examiner*—F. T. Moezie
*Attorney, Agent, or Firm*—James F. Tao; William G. Gosz

[57] ABSTRACT

A rodenticide composed of particulate zinc phosphide which has been encapsulated with a layer or coating of a thermoplastic polymer. This polymer coating will inhibit reaction, in the rodent's mouth so that the zinc phosphide will be consumed without the rodent detecting its' presence. However, the coating will allow reaction of the zinc phosphide in the rodent's stomach which will cause the death of the rodent.

10 Claims, No Drawings

ENCAPSULATED EFFICACIOUS ZINC PHOSPHIDE RODENTICIDE

BACKGROUND OF THE INVENTION

This invention relates to an efficacious and safe method of controlling rodent population. Rodents, especially Norway rats commmon to the United States, roof rats, black rats, ground squirrels, prairie dogs, mountain beaver, etc., feed on a wide variety of foods. Rats, in particular, do a tremendous amount of damage by their eating habits, destroying agricultural crops, stored grain and stored produce, as well as contributing to the spread of disease through their infestation of urban areas. Attempts to control or eliminate rodents have been made for many years. Because the rodents quickly learn to avoid the poisons and poison impregnated foods, the use of poisoned food or baits as practiced to date does not provide a long term solution to the rodent problem.

The need for economical rodent control methods for agricultural, commensal and industrial uses, necessitates a material that can be easily dispersed in the fields or in buildings and provide an efficacious long term method of rodent control. Many of the baits depend upon the impregnation of seeds, fruits, peanut butter, etc. with a poison. The rodents quickly learn to avoid such poison bait by the odor or taste, particularly when the discomfort of the ingestion of a sub-lethal quantity is associated with the bait. Therefore, it is advantageous to prepare a poison that has its odor and taste effectively masked and the onset of the reaction to the poison is delayed until a lethal amount is consumed and the rodent has left the bait area.

Attempts to encapsulate rodenticides have been made but generally enough rodenticide is entrapped in the encapsulating material or will permeate through it to allow the rodent to identify the fact that a poison is present. Also, methods have been developed to prepare enteric coated rodenticides, e.g. U.S. Pat. No. 2,957,804 wherein the rodenticide is surrounded by a resin material that will not dissolve in the acidic conditions of the stomach, but dissolves in the alkaline condition of the rodent's intestines. The theory is that the rodent that has eaten the poison would not realize that it was deadly since there would be considerable time delay from the ingestion to death, and thus would not avoid the enteric coated material. The efficacy of such encapsulated material has been shown to be no more than unencapsulated material because the amount of encapsulant needed to mask the material also decreases its availability as a poison.

Zinc phosphide ($Zn_3P_2$) is an efficient rodenticide in an acidic environment because it releases phosphine, a deadly poison. It is effective against many species of rodents. It suffers from the disadvantage that rodents easily identify it in a bait and avoid it. Zinc phosphide is considered one of the safest rodenticides to control rats and mice because of its emetic properties and the fairly rapid dissipation of the poison in the rodent's body. Thus, children, domestic animals, etc. will regurgitate the poison before it is lethal, whereas rodents cannot regurgitate. Zinc phosphide in the body of a dead rodent reacts with the fluids in the rodent's body and is consumed in a way which eliminates the hazard of secondary poisoning of other animals who may eat the dead rodent. For this reason zinc phosphide has been widely used for controlling rodents in agriculture so as to protect rice, sugarcane and other growing plants against attack. In the western United States, for example, zinc phosphide has had wide-spread use to control ground squirrels, and the like.

OBJECTS OF THE INVENTION

An object of the invention is to provide a rodenticide composed of zinc phosphide that does not react or taste in the mouth of the rodent so as to avoid detection but yet will react with the acidic condition of the rodent's stomach to produce toxic phosphine. This is important because zinc phosphide does not react substantially in alkaline environments to produce phosphine.

Another object of this invention is to provide a coating which, if subjected to crushing, will not fracture in such a way as to expose the zinc phosphide.

SUMMARY OF THE INVENTION

These and other objects of the invention are accomplished by a rodenticide of this invention composed of zinc phosphide wherein the particles of zinc phosphide have been encapsulated with a layer or coating of a thermoplastic polymer capable of dissolving in the acid environment of a rodent's stomach. This polymer coating will not allow the moisture of the rodent's mouth to affect the zinc phosphide, but will allow the environment of the rodent's stomach to penetrate the coating and react with the phosphide thus generating phosphine to cause death of the rodent.

DETAILED DESCRIPTION OF THE INVENTION

Zinc phosphide ($Zn_3P_2$) is well known as a rodenticide being especially effective against rats and field mice. Zinc phosphide is a dark grey crystalline material with a faint garlic-like odor and is a very stable compound when stored in a dry state. It is substantially insoluble in water, but reacts with acid to produce phosphine, which is poisonous.

The thermoplastic polymers which may be successfully used in this invention must be capable of being removed in the acid environment of a rodent's stomach at least to the extent of exposing a lethal dose of the zinc phosphide. The lethal dose of this invention for Norway rats is approximately 30 mg. zinc phosphide per Kilogram of body weight of rodent. The thermoplastic polymers which are preferred for use in accordance with this invention are the polyamides, especially nylon 6, nylon 66, nylon 6-10 and nylon 612. However, others including nylons 1, 2, 3, 4, 5, 7, 8, 9, 10, 77 and substituted polyamides which have solubility characteristics rendering them suitable, depending upon the thickness of the coating applied, may be used.

There are many techniques that may be used for coating the thermoplastic polymer onto the rodenticide, such as pan coating, spraying onto moving particles, spray drying, solvent evaporation, belt coating and others. The selection of the coating technique will be dependent upon the variables associated with the polymer, e.g. economies, quality, equipment available etc. A preferred method is to dissolve the polymer in a suitable solvent, which solvent will not dissolve or react with the zinc phosphide. The solvent is removed from the slurry of zinc phosphide in the solution by evaporation.

EXAMPLES

The following examples are given to further illustrate the invention; however, they are not intended to limit the scope thereof except as defined by the appended claims.

EXAMPLE 1

In a 600 cc beaker equipped with stirrer is placed 300 cc of dimethylformamide, 60 grams of zinc phosphide and 3 grams of nylon 6, a linear polymer obtained by polymerization of caprolactam, and stirred while heated to reflux (150° C.) until the nylon is in solution. While stirring, the mixture is warmed allowing the dimethylformamide to evaporate leaving the nylon 6 coated upon the zinc phosphide. One percent of this product was formulated into an EPA placebo and was found effective in killing mice.

EXAMPLE 2

In a 2-liter resin flask reactor, equipped with stirrer, is placed 1800 ml dimethylformamide, 500 grams zinc phosphide and 25 grams nylon 6–12. The mixture is stirred and heated to reflux (150° C.) to dissolve the nylon. The excess dimethylformamide is then distilled off under vacuum at approximately 60° C. After most of the dimethylformamide is distilled off, the temperature is increased to 175° C. with continued agitation. The solids go through a pasty consistency and then becomes a flowing powder, as the last of the solvent is evaporated. The vapor space was purged with nitrogen to remove the last traces of solvent. A yield of 514 grams of free-flowing 5% by weight nylon coated zinc phosphide was obtained.

A sample of the material recovered from Example 2 was formulated into a bait using EPA Placebo. The bait was fed to Norway rats under choice test conditions in which a bowl of unpoisoned placebo and a bowl of placebo treated with rodenticide of this invention were placed in the cage with the rat under test. 100% of the rats were dead on the second day demonstrating the efficacy of the rodenticide of this invention.

Table I shows the results obtained by varying the weight % add-on of nylon 6–12 on the zinc phosphide as well as the weight % zinc phosphide added to the EPA Placebo. Mortality is reported in number of rats killed per number of rats tested and also is reported in percent of rats killed. Bait acceptance is reported in accordance with the formula given at the end of the Table.

TABLE I

ENCAPSULATED ZINC PHOSPHIDE ($Zn_3P_2$)
AS RODENTICIDE
Choice Tests - Domestic Rats

| % Add-on of Nylon 6-12 | Mortality # of rats | % | % Bait Acceptance |
|---|---|---|---|
| 1% $Zn_3P_2$ in EPA vs. EPA Placebo | | | |
| Unencapsulated | 5/10 | 50 | 3 |
| 2 | 18/20 | 90 | 26 |
| 3.5 | 9/10 | 90 | 34 |
| 5 | 20/20 | 100 | 44 |
| 10 | 9/10 | 90 | 12 |
| Mean of Encapsulated Data | 56/60 | 93 | 31 |
| 2% $Zn_3P_2$ in EPA vs. EPA Placebo | | | |
| Unencapsulated | 3/10 | 30 | 3 |
| 2 | 5/5 | 100 | 22.3 |
| 3.5 | 5/5 | 100 | 61 |
| 5 | 5/5 | 100 | 59 |
| Mean of Encapsulated Data | 15/15 | 100 | 47 |

$$\% \text{ Bait Acceptance} = \frac{\text{Wt. } Zn_3P_2 \text{ Bait Consumed}}{\text{Total Wt. Food Consumed}} \times 100$$

<30% = Bait Avoidance
>70% = Bait Preference

From Table I it can be observed that the 93% mortality of rats due to the encapsulated 1% zinc phosphide treated bait is significantly greater than the 50% observed from the unencapsulated zinc phosphide. Further, at 2% zinc phosphide-treated bait the 100% mortality of rats is even greater than the 30% mortality for unencapsulated zinc phosphide.

The % bait acceptance shows no bait avoidance at 3.5% to 5% nylon 6–12 coating on zinc phosphide whereas there was significant avoidance of the unencapsulated zinc phosphide-treated bait.

While I have shown and described particular embodiments of the invention, modifications and variations thereof will occur to those skilled in the art. I wish it to be understood, therefore, that the appended claims are intended to cover such modifications and variations which are within the true scope and spirit of my invention.

What is claimed is:

1. A rodenticide comprising a lethal amount of zinc phosphide coated with a thermoplastic polyamide polymer which allows phosphine to be released in the stomach of the rodent due to reaction between the acidic liquid in the stomach and the zinc phosphide, said polyamide polymer being present in the range of from about 2% of about 10% by weight of zinc phosphide.

2. The rodenticide of claim 1, wherein the polyamide polymer is a nylon polymer.

3. The rodenticide of claim 2, wherein the nylon polymer is nylon 6–12.

4. The rodenticide of claim 2, wherein the nylon polymer is nylon 66.

5. The rodenticide of claim 2, wherein the nylon polymer is nylon 6.

6. A rodenticide comprising a lethal amount of encapsulated zinc phosphide and an extender further comprising a bait or rodent attractant, said zinc phosphide being coated with a nylon polymer which allows phosphine to be released in the stomach of the rodent due to the reaction between the acidic liquid in the stomach and the zinc phosphide, said nylon polymer being present in the range of from about 2% to about 10% by weight of zinc phosphide.

7. A rodenticide of claim 6, wherein the nylon polymer is nylon 6–12.

8. The rodenticide of claim 6, wherein the nylon polymer is nylon 66.

9. The rodenticide of claim 6, wherein the nylon polymer is nylon 6.

10. The rodenticide of claim 9, wherein the nylon 6–12 is 5% by weight of the zinc phosphide.

* * * * *